(12) United States Patent
Sorajja (10) Patent No.: US 10,369,357 B2
(45) Date of Patent: Aug. 6, 2019

(54) PERCUTANEOUS TEMPORARY EPICARDIAL PACEMAKER SYSTEM

(71) Applicant: Mayo Foundation for Medical Education and Research, Rochester, MN (US)

(72) Inventor: Dan Sorajja, Phoenix, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 34 days.

(21) Appl. No.: 15/328,124

(22) PCT Filed: Jul. 22, 2015

(86) PCT No.: PCT/US2015/041518
§ 371 (c)(1),
(2) Date: Jan. 23, 2017

(87) PCT Pub. No.: WO2016/014656
PCT Pub. Date: Jan. 28, 2016

(65) Prior Publication Data
US 2017/0209691 A1    Jul. 27, 2017

Related U.S. Application Data

(60) Provisional application No. 62/028,584, filed on Jul. 24, 2014.

(51) Int. Cl.
| A61N 1/05 | (2006.01) |
| A61N 1/39 | (2006.01) |
| A61N 1/362 | (2006.01) |
| A61N 1/04 | (2006.01) |

(52) U.S. Cl.
CPC .......... *A61N 1/0595* (2013.01); *A61N 1/046* (2013.01); *A61N 1/0492* (2013.01); *A61N 1/0502* (2013.01); *A61N 1/0587* (2013.01); *A61N 1/3625* (2013.01); *A61N 1/39* (2013.01); *A61N 1/3962* (2013.01)

(58) Field of Classification Search
CPC .. A61N 1/0595; A61N 1/3625; A61N 1/0502; A61N 1/046; A61N 1/0492; A61N 1/39; A61N 1/0587
See application file for complete search history.

(56) References Cited

U.S. PATENT DOCUMENTS

| 3,602,471 A * | 8/1971 | Reed, III | ................. B64D 1/02 248/156 |
| 4,321,931 A * | 3/1982 | Hon | ..................... A61B 5/0444 600/376 |
| 5,571,163 A | 11/1996 | Helland | |

(Continued)

OTHER PUBLICATIONS

International Search Report and Written Opinion in International Application No. PCT/US2015/041518, dated Oct. 15, 2015, 15 pages.

(Continued)

*Primary Examiner* — Mark Bockelman
(74) *Attorney, Agent, or Firm* — Fish & Richardson P.C.

(57) ABSTRACT

This document provides devices and methods for the treatment of heart conditions. For example, this document provides a percutaneous temporary epicardial pacemaker device and system for treating heart arrhythmia.

10 Claims, 7 Drawing Sheets

(56) References Cited

U.S. PATENT DOCUMENTS

| | | | |
|---|---|---|---|
| 5,928,191 A | 7/1999 | Houser et al. | |
| 6,330,481 B1* | 12/2001 | Van Wijk | A61N 1/0587 |
| | | | 607/129 |
| 7,288,096 B2* | 10/2007 | Chin | A61B 17/3468 |
| | | | 606/108 |
| 8,768,490 B2* | 7/2014 | Weitzig | A61N 1/056 |
| | | | 607/122 |
| 2009/0054964 A1 | 2/2009 | Osypka | |
| 2011/0071584 A1* | 3/2011 | Mokelke | A61N 1/3625 |
| | | | 607/4 |
| 2016/0128599 A1* | 5/2016 | Rea | A61B 5/04001 |
| | | | 600/546 |

OTHER PUBLICATIONS

International Preliminary Report on Patentability in International Application No. PCT/US2015/041518, dated Feb. 2, 2017, 8 pages.

* cited by examiner

PERCUTANEOUS TEMPORARY EPICARDIAL PACEMAKER SYSTEM

CROSS REFERENCE TO RELATED APPLICATIONS

This application is a National Stage application under 35 U.S.C. § 371 of International Application No. PCT/US2015/041518, having an International Filing Date of Jul. 22, 2015, which claims the benefit of U.S. Provisional Ser. No. 62/028,584 filed Jul. 24, 2014. This disclosure of the prior application is considered part of (and is incorporated by reference in) the disclosure of this application.

BACKGROUND

1. Technical Field

This document relates to devices and methods for the treatment of heart conditions. For example, this document relates to a percutaneous temporary epicardial pacemaker device and system for treating heart arrhythmia.

2. Background Information

Patients with bradyarrhythmia may experience symptoms including dyspnea, lightheadedness, fatigue, presyncope, or syncope. The etiology of bradyarrhythmia is often sinus node dysfunction or a conduction disturbance. Some patients may have a transient cause of bradyarrhythmia such as electrolyte abnormalities or medication overdose. However, other patients have intrinsic conduction disease with conduction block occurring below the Bundle of His, and as such the heart beat is erratic, unstable, and unreliable.

For treatment, as part of advanced cardiac life support algorithms, patients are given atropine, which is generally ineffective for both transplanted hearts or in conduction disturbances that below the Bundle of His. Another treatment commonly given is a chronotropic agent such as dopamine or epinephrine.

If these medications fail to provide an adequate remedy, then transcutaneous pacing may be tried. Transcutaneous pacing is most commonly delivered by defibrillator pads applied to "anterior/posterior" or "right chest/left axilla" locations of the patients. The defibrillator is then able to pace the patient's heart using high energy in its pacing mode. This pacing may be uncomfortable for many patients, as it results in skeletal muscle contractions synchronous with the pacing. The effectiveness of the pacing is limited by contact of the defibrillator pads with the skin (such as by hair), larger body habitus, and COPD which limit the current delivery to the heart.

If transcutaneous pacing fails to provide an adequate remedy, then transvenous pacing may be tried. Placement of a temporary pacemaker wire transvenously may require placement of a central line under fluoroscopy (with the requisite leaded apron protection and additional personnel such a radiology tech). Depending on the type of temporary pacemaker placed, there may be barriers to the placement, including technical expertise to achieve the placement, tricuspid regurgitation, and vein occlusion. The transvenous pacing lead may become dislodged after completion of the placement procedure, and this requires additional fluoroscopy to reposition the transvenous lead.

If there are no reversible etiologies for the symptomatic bradycardia or high-grade conduction disturbances, a permanent pacemaker is indicated. For patients with mild symptoms due to these etiologies, there is time to work through the above treatment options. However, some patients have more severe symptoms and require more immediate treatment than allowable for placement of transvenous pacing systems, or they have more discomfort than necessary from the transcutaneous pacing pads.

SUMMARY

This document provides devices and methods for the treatment of heart conditions. For example, this document provides a percutaneous temporary epicardial pacemaker device and system for treating heart arrhythmia.

In one implementation, a pacemaker device includes an electrode assembly including an electrode positioned at a distal end of the electrode assembly; a handle; and an adjustment mechanism whereby the electrode can be axially extended and axially retracted in relation to the handle.

Such a pacemaker device may optionally include one or more of the following features. The adjustment mechanism may include a rotary adjustment knob, and rotation of the rotary adjustment knob may axially extend and axially retract the electrode in relation to the handle. The rotary adjustment knob may be adjacent to a proximal end of the handle. The pacemaker device may further comprise a flange fixedly attached to a distal end portion of the handle. The pacemaker device may further comprise a releasable lock that is configured to fix the adjustment mechanism in a desired position. The handle may include one or more helical grooves defined within a wall of the handle. The electrode assembly may include one or more pins that are each slidably received within one of the one or more helical grooves. The pacemaker device may further comprise an inner sleeve assembly disposed within the handle and configured to receive at least a portion of the electrode assembly. The adjustment mechanism may include a telescoping arrangement, and manipulation of the telescoping arrangement may axially extend and axially retract the electrode in relation to the handle.

In another implementation, a pacemaker system includes a pacemaker device; a transcutaneous electrode patch; and an external automatic cardioverter defibrillator. The pacemaker device includes an electrode assembly including an electrode positioned at a distal end of the electrode assembly; a handle; and an adjustment mechanism whereby the electrode can be axially extended and axially retracted in relation to the handle.

In another implementation, a method for treating bradyarrhythmia of a patient includes percutaneously installing a pacemaker device such that a distal portion of the pacemaker device including an electrode is position subcutaneously within the patient and a proximal portion of the pacemaker device is positioned externally of the patient; and providing pacing energy to the patient via the pacemaker device.

Such a method for treating bradyarrhythmia of a patient may optionally include one or more of the following features. The method may further comprise attaching a transcutaneous electrode to the patient and pacing via the electrode of the pacemaker device and the transcutaneous electrode. The method may further comprise adjusting a depth of the electrode in relation to a skin surface of the patient.

Particular embodiments of the subject matter described in this document can be implemented to realize one or more of the following advantages. First, in some embodiments heart conditions such as bradyarrhythmia and others can be treated using the devices and methods provided herein. Second, the use of the percutaneous temporary epicardial pacemaker systems provided herein may result in less pain to the patient as compared to some transcutaneous pacing techniques. That may be the case for example, because the position of the pacing electrode of the pacemaker devices provided herein can be placed distal to the skeletal muscle, thereby avoiding the discomfort from muscle contractions due to pacing stimuli. In addition, in some cases a lower amount of energy may be needed to operate the pacemaker devices provided herein as compared to some transcutaneous pacing systems, because the pacing electrode can be positioned closer to the heart than transcutaneous pacing systems. Third, no fluoroscopy is required to place the pacemaker devices provided herein, in contrast to some transvenous pacing systems. Fourth, certain functional limitations such as tricuspid regurgitation and vein occlusion may not apply to the pacemaker devices provided herein because they do not pass through the tricuspid valve or venous systems. Fifth, the position of the electrode of the pacemaker devices provided herein can be readily adjusted to a closer position to the heart for improved capture thresholds. Sixth, in some embodiments the pacemaker devices provided herein can be deployed in a short time period (e.g., within one minute in some circumstances). Seventh, in some implementations the pacemaker devices provided herein are deployable through a small incision in the skin. Such a minimally invasive technique can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices and methods for the treatment of heart conditions. For example, this document provides a percutaneous temporary epicardial pacemaker device and system for treating heart arrhythmia.

Figure 1A:
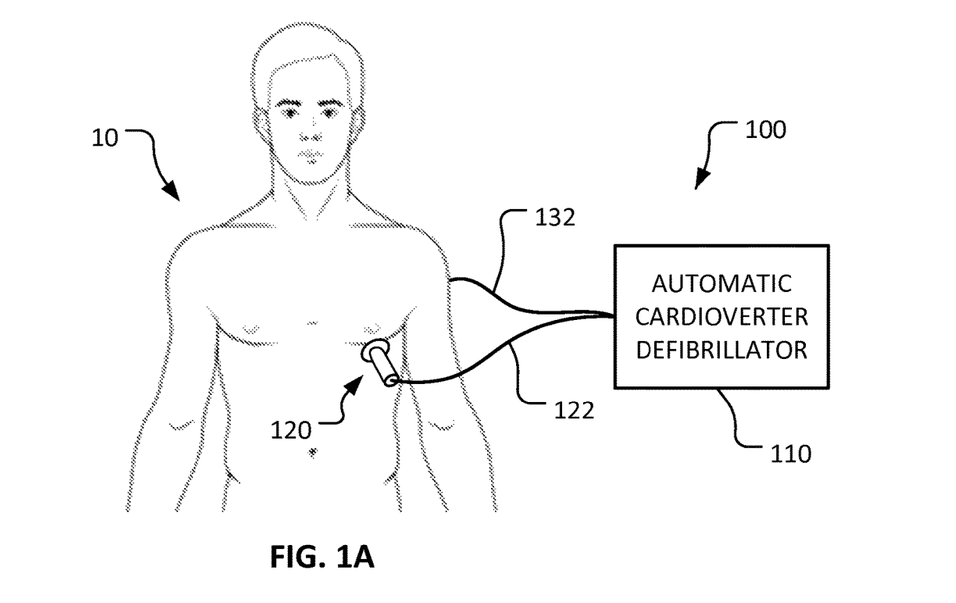
FIG. 1A is an anterior view of a patient that is being treated using percutaneous temporary epicardial pacemaker system in accordance with some embodiments provided herein.
Figure 1B:
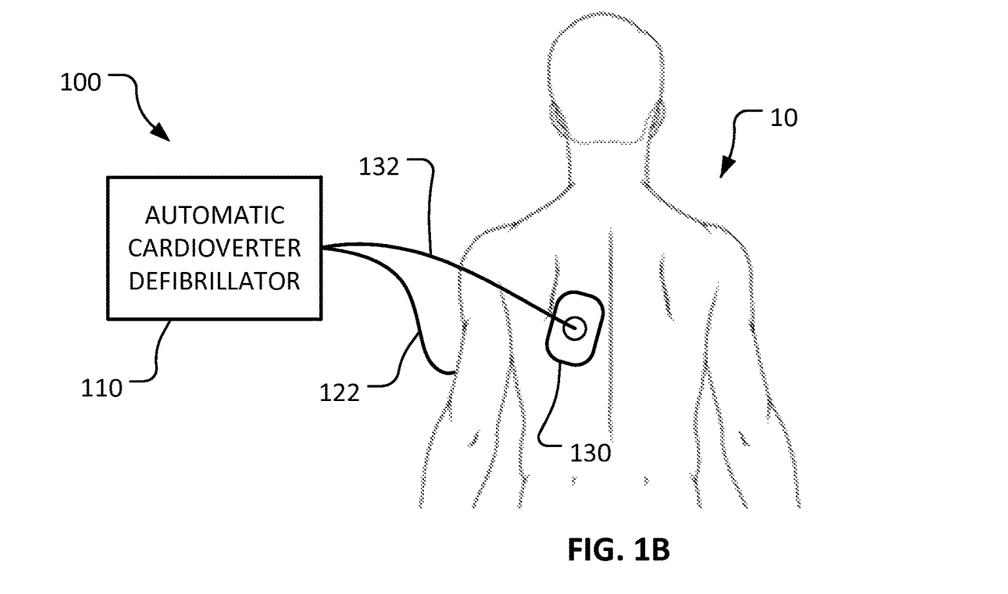
FIG. 1B is a posterior view of the patient and the percutaneous temporary epicardial pacemaker system of FIG. 1A.

Referring to FIGS. 1A and 1B, a patient 10 is shown being treated by an example percutaneous temporary epicardial pacemaker system 100 in accordance with some embodiments. In the depicted embodiment, percutaneous temporary epicardial pacemaker system 100 includes an external automatic cardioverter defibrillator 110, an example percutaneous temporary epicardial pacemaker device 120 (hereinafter "pacemaker device 120"), and a transcutaneous electrode patch 130. Pacemaker device 120 is percutaneously attached to patient 10. That is, as explained further below, a distal portion of pacemaker device 120 is positioned subcutaneously while a proximal portion of pacemaker device 120 is located external of patient 10. Transcutaneous electrode patch 130 is attached to the skin surface of patient 10. Percutaneous temporary epicardial pacemaker system 100 can provide pacing to the heart of patient 10 to treat bradyarrhythmia.

While in the depicted arrangement, pacemaker device 120 and transcutaneous electrode patch 130 are shown attached to patient 10 in particular locations, it should be understood that the implementation of percutaneous temporary epicardial pacemaker system 100 is not limited to such an arrangement. In the depicted arrangement, pacemaker device 120 is the negative electrode, and transcutaneous electrode patch 130 is the positive electrode. In this arrangement, pacemaker device 120 is positioned on the chest of patient 10 below the left breast in line with the left nipple, and transcutaneous electrode patch 130 is positioned on the left posterior chest of patient 10 beneath the scapula and lateral to the spine. In some implementations, pacemaker device 120 is positioned on other locations on patient 10 in relation to the transcutaneous electrode patch 130, in order to optimally position the heart between the pacemaker device 120 and transcutaneous electrode patch 130. For example, in some implementations pacemaker device 120 is positioned more laterally in the axially line under the armpit, with the transcutaneous electrode patch 130 positioned near the anterior right shoulder.

Automatic cardioverter defibrillator 110 is a commercial device that may be obtained from manufacturers such as Physio-Control Corporation, Philips Healthcare, Zoll Medical Corporation, and others. The depicted automatic cardioverter defibrillator 110 unit has an external pacing capability to allow external pacing of bradycardias using pacemaker device 120 and transcutaneous electrode patch 130. Automatic cardioverter defibrillator 110 is electrically coupled to pacemaker device 120 via a pacemaker lead 122. Automatic cardioverter defibrillator 110 is also electrically coupled to transcutaneous electrode patch 130 via a patch lead 132.

Transcutaneous electrode patch 130 is a commercial device that may be obtained from manufacturers such as Zoll Medical Corporation, Philips Healthcare, and others. In some embodiments, transcutaneous electrode patch 130 includes both ECG monitoring and pacing electrodes in a single pad assembly, while other embodiments have ECG monitoring via separate ECG electrodes independent of the transcutaneous electrode patch 130.

Figure 2A:
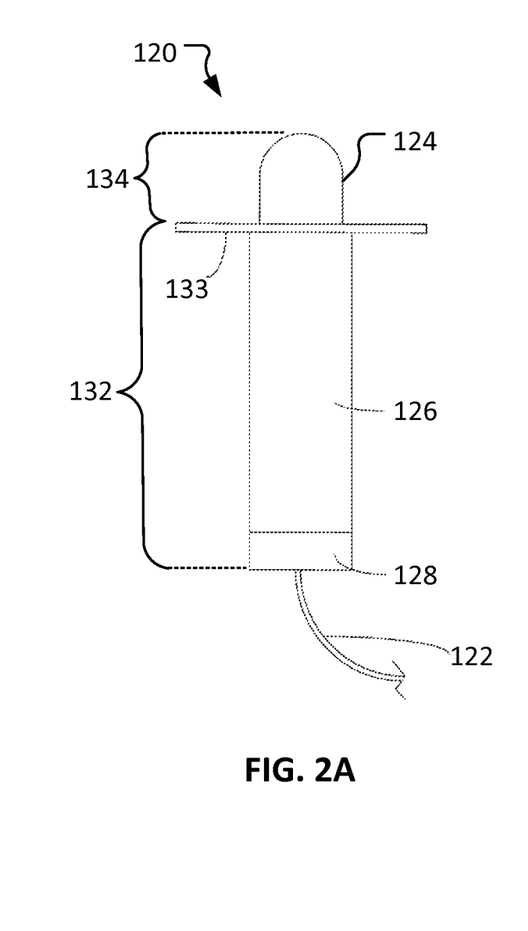
FIG. 2A is a side view of a percutaneous temporary epicardial pacemaker device in accordance with some embodiments provided herein.
Figure 2B:
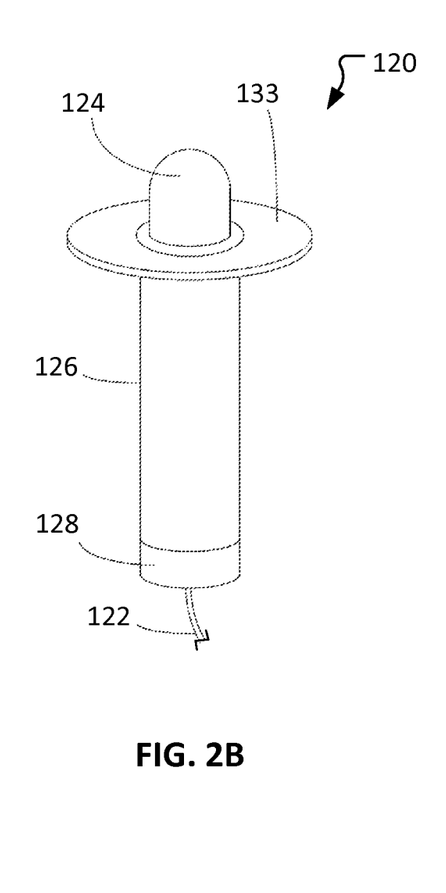
FIG. 2B is a perspective view of the percutaneous temporary epicardial pacemaker device of FIG. 2A.

Referring also to FIGS. 2A and 2B, pacemaker device 120 includes pacemaker lead 122, an electrode 124, a handle 126, an electrode depth rotary adjustment knob 128, and a flange 133. As will be described further below, electrode 124 is an electrically conductive component that is electrically coupled to pacemaker lead 122. That is, electrode 124 is the active element of pacemaker device 120 in that it provides the pacing functionality. In some embodiments, other portions of pacemaker device 120 are electrically isolated from pacemaker lead 122 and electrode 124.

In general, pacemaker device 120 includes a proximal portion 132 and a distal portion 134. In use, distal portion 134 is positioned subcutaneously in relation to patient 10, whereas proximal portion 132 is positioned externally to patient 10. In some implementations, flange 133 is positioned externally adjacent to the skin of patient 10. Hence, pacemaker device 120 is percutaneously installed onto patient 10 through a small incision (e.g., just large enough to pass electrode 124 therethrough).

Briefly, electrode 124 can be axially extended and retracted in relation to handle 126 by manipulation of electrode depth rotary adjustment knob 128. In the depicted embodiment, a rotation of rotary adjustment knob 128 causes electrode 124 to be axially extended and retracted in relation to handle 126. More particularly, a rotation in a first direction causes electrode 124 to be axially extended, and a rotation in a second direction that is opposite of the first direction causes electrode 124 to be axially retracted. By manipulating the rotary adjustment knob 128, a clinician operator can position electrode 124 at a desired subcutaneous depth within patient 10. In some embodiments, other mechanical or electro-mechanical configurations can be used for adjustment of the depth of electrode 124. For example, non-rotary adjustment mechanisms may be used in other embodiments, such as telescoping components within the handle 126 to manipulate the depth of the electrode 124.

FIGS. 3 through 8B exemplify some componentry and an assembly arrangement for one particular example embodiment of pacemaker device 120. It should be understood that additional pacemaker device embodiments with other types of components and assembly arrangements are also envisioned within the scope of this disclosure.

Figure 3:
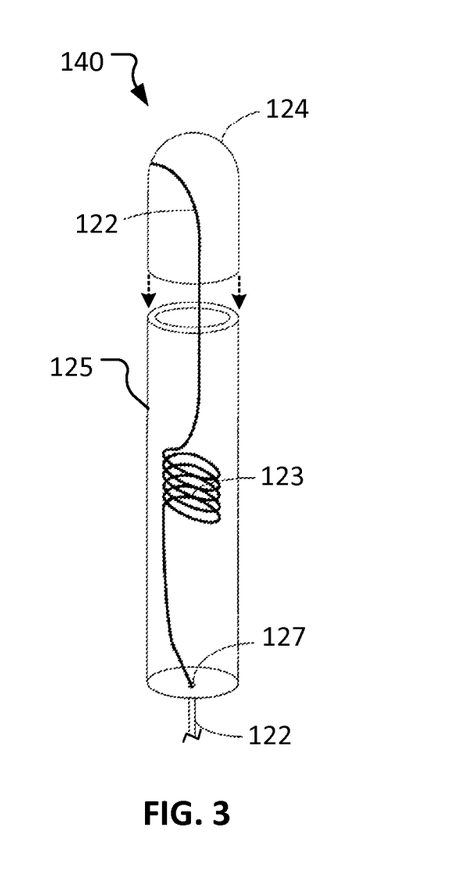
FIG. 3 is a transparent exploded perspective view of an electrode assembly for use with the percutaneous temporary epicardial pacemaker device of FIGS. 2A and 2B.
Figure 4A:
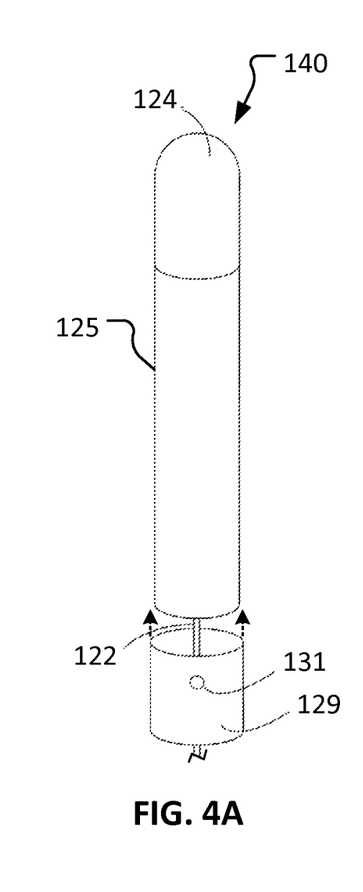
FIG. 4A is an exploded perspective view of the electrode assembly of FIG. 3 and an end cap in accordance with some embodiments provided herein.
Figure 4B:
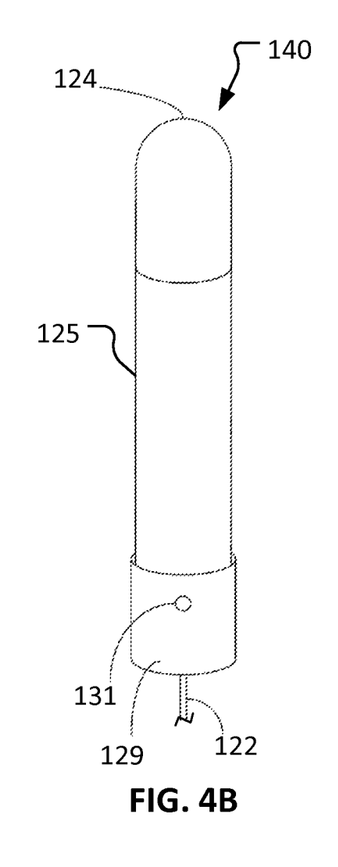
FIG. 4B is a perspective view of the electrode assembly and end cap of FIG. 4A in an assembled configuration.

Referring now to FIGS. 3, 4A and 4B, an electrode assembly 140 includes electrode 124, a barrel 125, and an end cap 129. Electrode 124 extends from a distal end of barrel 125, and end cap 129 is fixedly positioned on a proximal end of barrel 125. While electrode 124 is electrically conductive and activated via pacemaker lead 122, the other portions of electrode assembly 140 can be electrically isolated from electrode 124.

In FIG. 3, electrode 124 and barrel 125 are transparently shown so that the routing of pacemaker lead 122, and an extendable lead portion 123 of pacemaker lead 122, are readily visible. Extendable lead portion 123 facilitates a fixed relationship between pacemaker lead 122 and handle 126. That is, as electrode assembly 140 is extended or retracted in relation to handle 126, extendable lead portion 123 extends or retracts to take up resulting slack of electrode lead 122. In the depicted embodiment, extendable lead portion 123 is a coil. In some embodiments, other configurations may be used for extendable lead portion 123 such as, but not limited to, a festooned portion, electrical brushes, a slack portion, and the like.

Barrel 125 includes a proximal opening 127 that can slidably transmit electrode lead 122 therethrough. In some alternative embodiments, extendable lead portion 123 is omitted and pacemaker lead 122 slides in relation to handle 126.

In the depicted embodiment, end cap 129 is fixedly coupled onto barrel 125. End cap 129 includes one or more pins 131 that radially project from end cap 129. In the depicted embodiment, two pins 131 (only one of which is visible in these views) positioned about 180° opposite from each other are included on end cap 129. In some embodiments, other types of pins or other types of mechanical features can be included as alternatives to pins 131. As will be explained further below, the position of electrode assembly 140 can be controlled by controlling the position of pins 131.

Figure 5A:
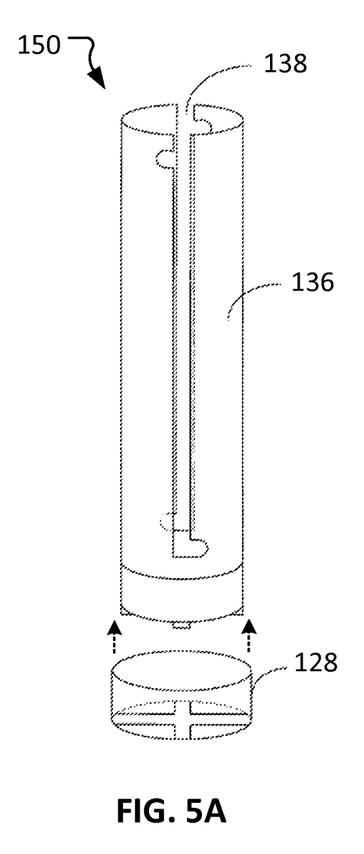
FIG. 5A is an exploded perspective view of an inner sleeve and a rotary adjustment knob for use with the percutaneous temporary epicardial pacemaker device of FIGS. 2A and 2B.
Figure 5B:
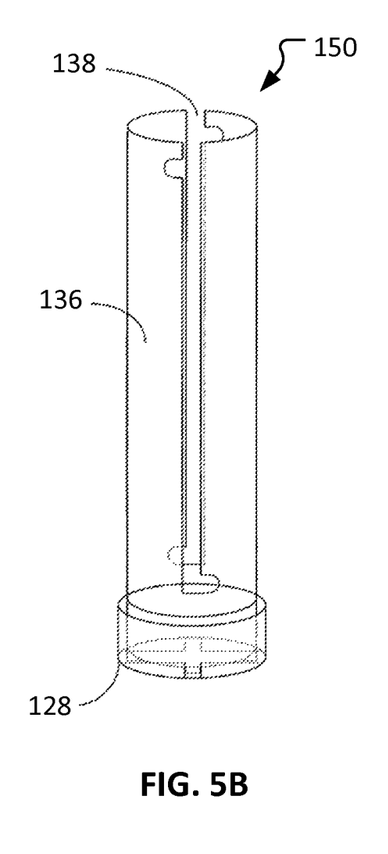
FIG. 5B is a perspective view of the inner sleeve and rotary adjustment knob of FIG. 5A in an assembled configuration.

Referring to FIGS. 5A and 5B, an inner sleeve assembly 150 includes an inner sleeve 136 and rotary adjustment knob 128. In the depicted embodiment, rotary adjustment knob 128 is fixedly attached to the proximal end of inner sleeve 136. The distal end of inner sleeve 136 is open and configured to slidably receive electrode assembly 140 therein, as will be described further below. Inner sleeve 136 includes one or more slots 138. In the depicted embodiments, inner sleeve 136 includes two slots 138 that are positioned about 180° opposite from each other. Slots 138 are configured to slidably receive pins 131 of electrode assembly 140 therein.

Rotary adjustment knob 128 is configured to be manipulated by manual rotation. In some embodiments, rotary adjustment knob 128 includes a surface texture or surface features that facilitate gripping and manipulation of rotary adjustment knob 128. When rotary adjustment knob 128 is rotated, inner sleeve 136 also rotates because rotary adjustment knob 128 is fixedly attached to inner sleeve 136. In some embodiments, a lock or latch device is included by which rotary adjustment knob 128 can be releasably fixed in a desired position.

Figure 6A:
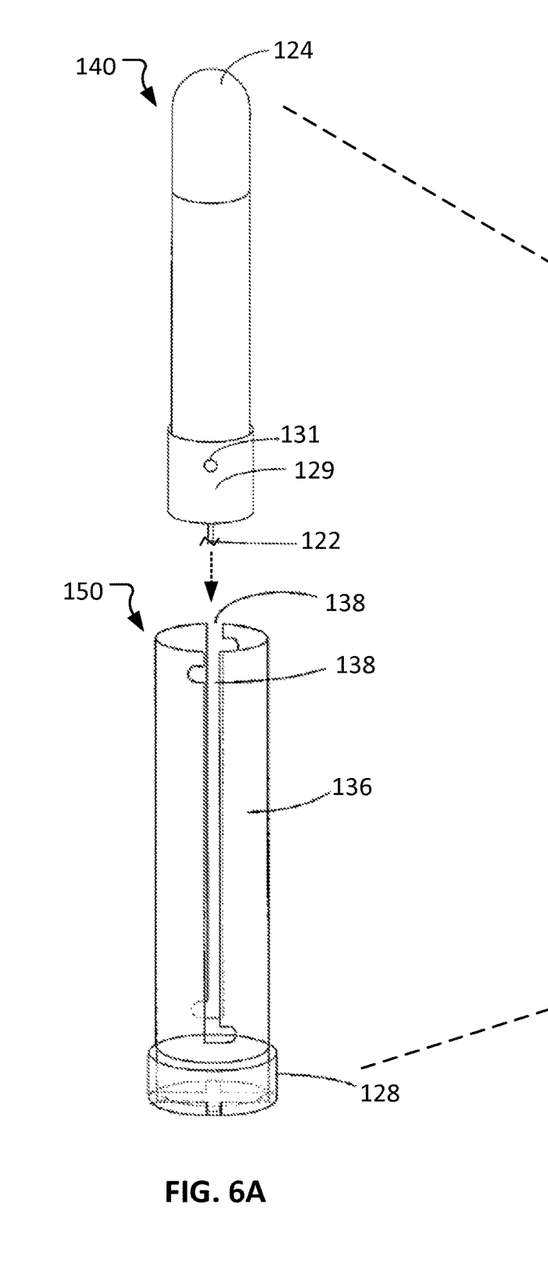
FIG. 6A is an exploded perspective view of the electrode assembly and end cap of FIG. 4B and the inner sleeve and rotary adjustment knob of FIG. 5B.
Figure 6B:
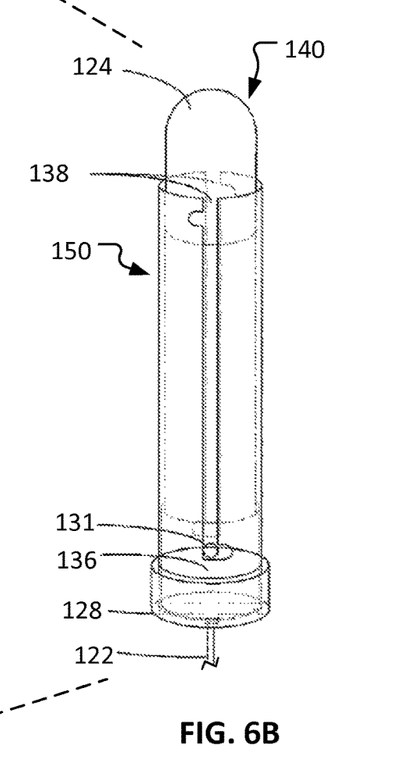
FIG. 6B is a perspective view showing the components of FIG. 6A in an assembled configuration.

Referring to FIGS. 6A and 6B, electrode assembly 140 can be slidably received in inner sleeve assembly 150. Pins 131 are slidably received in slots 138. Electrode lead 122 extends through an opening in rotary adjustment knob 128. Rotation of rotary adjustment knob 128 causes rotation of electrode assembly 140 and of inner sleeve assembly 150, while electrode assembly 140 remains free to slide axially within inner sleeve assembly 150.

In the configuration shown in FIG. 6B, electrode assembly 140 is in its fully retracted position. As will be described further below, electrode assembly 140 can be slidably extended from inner sleeve assembly 150 as desired by a clinician operator.

Figure 7A:
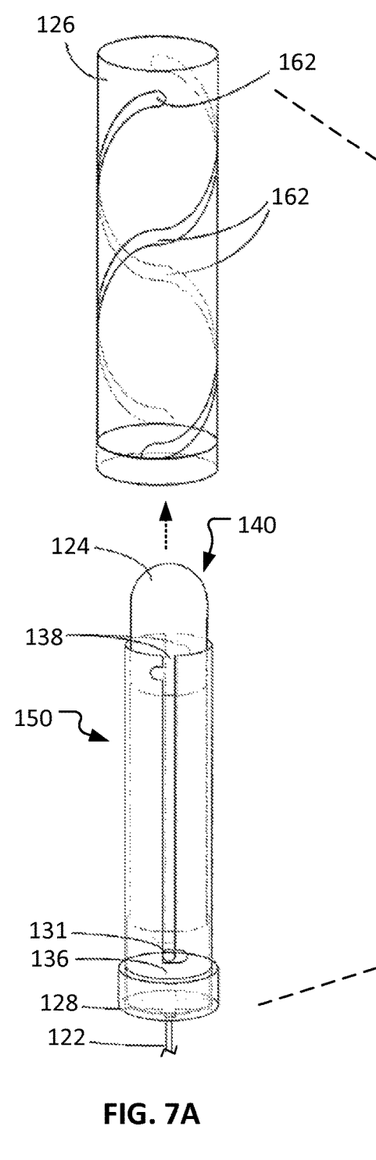
FIG. 7A is an exploded perspective view of the assembly of FIG. 6B and an outer casing handle for use with the percutaneous temporary epicardial pacemaker device of FIGS. 2A and 2B.
Figure 7B:
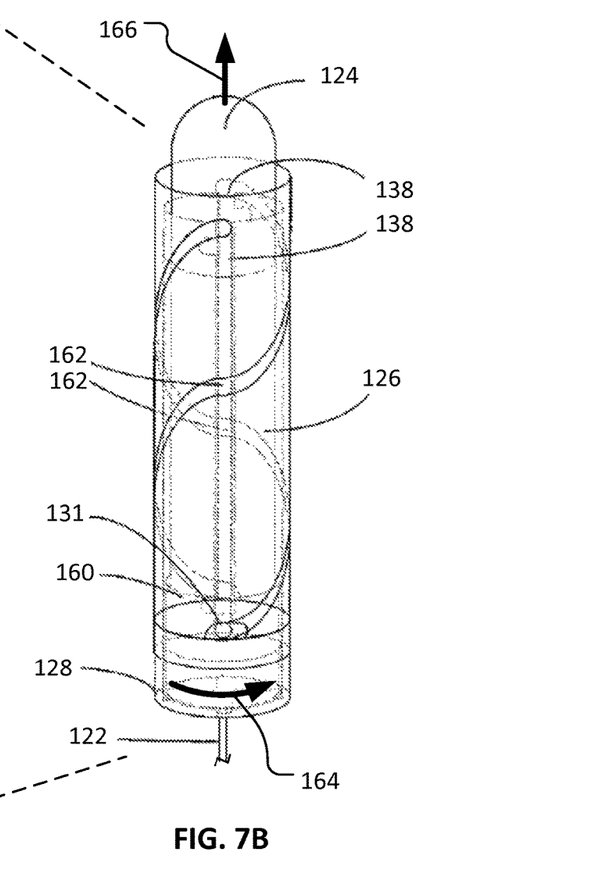
FIG. 7B is a perspective view showing the components of FIG. 7A in an assembled configuration.

Referring to FIGS. 7A and 7B, the combination of electrode assembly 140 positioned within inner sleeve assembly 150 can be slidably received within an outer casing handle 126. In these illustrations, handle 126 is shown transparently so that one or more channels 162 therein can be visualized. In the depicted embodiment, handle 126 includes two channels 162. Channels 162 are generally helical grooves that are open in the cylindrical interior space defined by handle 126. However, channels 162 do not extend through to the outer diameter of handle 126. Rather, channels 162 terminate in the wall thickness of handle 126.

Handle 126 includes open proximal and distal ends that are configured to slidably receive the combination of electrode assembly 140 and inner sleeve assembly 150 therein. When so assembled, rotary adjustment knob 128 is adjacent to and generally abuts the proximal end of handle 126, and electrode 124 extends distally beyond the distal end of handle 126.

Channels 162 are configured to slidably receive pins 131 therein. In this configuration, manual rotation of rotary adjustment knob 128 causes pins 131 to follow the paths defined by channels 162. Therefore, for example, a rotation of rotary adjustment knob 128 in the direction indicated by arrow 164 will cause an axial extension of electrode 124 in the direction indicated by arrow 166. After electrode 124 has been so extended from the configuration shown in FIG. 7B, a rotation of rotary adjustment knob 128 in the direction opposite of the direction indicated by arrow 164 will cause an axial retraction of electrode 124 in the direction opposite of the direction indicated by arrow 166. In this manner, a clinician operator can extend or retract electrode 124 in relation to handle 126. Such an extension or retraction of electrode 124 can be performed while pacemaker device 120 is percutaneously installed on patient 10 (refer to FIGS. 1A and 1B), and/or while pacemaker device 120 is completely exterior to patient 10.

Figure 8A:
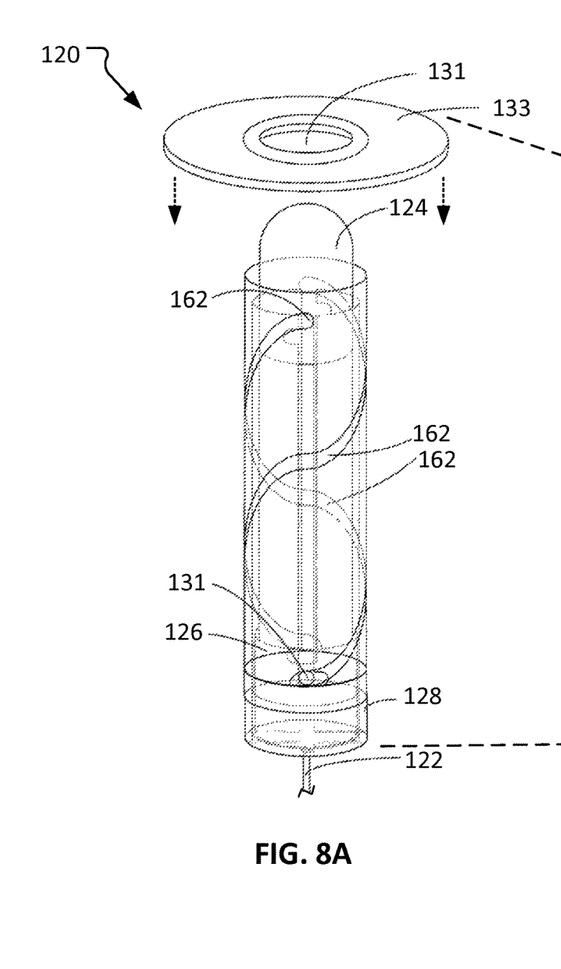
FIG. 8A is an exploded perspective view of the assembly of FIG. 7B and a flange for use with the percutaneous temporary epicardial pacemaker device of FIGS. 2A and 2B.
Figure 8B:
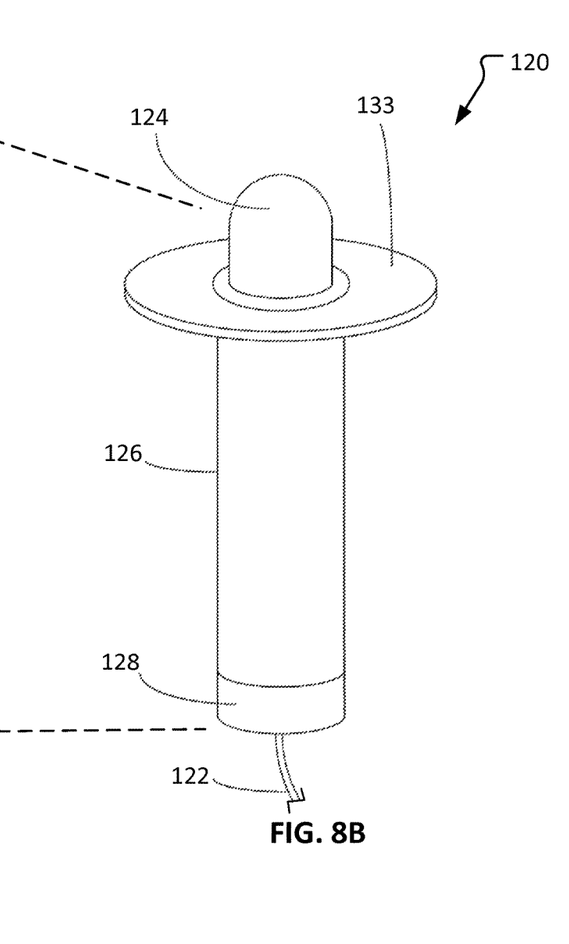
FIG. 8B is a perspective view showing the components of FIG. 8A in an assembled configuration.

Referring to FIGS. 8A and 8B, flange 133 can be fixedly attached to handle 126. Flange 133 defines a central opening 131 through which electrode 124 can freely extend. While in the depicted embodiment, flange 133 is circular, in some embodiments other shapes such as, but not limited to, ovular, rectangular, and the like can be used.

In some embodiments, flange 133 includes features and/or shapes to facilitate attachment of pacemaker device 120 to patient 10. For example, in some embodiments flange 133 includes holes or other features by which sutures can be engaged with flange 133. In some embodiments, flange 133 may include adhesive strips or an adhesive coating, and the like.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A pacemaker device comprising:
    an electrode assembly including an electrode positioned at a distal end of an elongate barrel, wherein the electrode and the elongate barrel are electrically isolated from each other;
    one or more pins attached to and extending from the electrode assembly;
    an inner sleeve defining one or more longitudinal slots, wherein the electrode assembly is slidably positioned within the inner sleeve such that each of the pins extends through a respective one of the longitudinal slots;
    a rotary adjustment knob attached to a proximal end of the inner sleeve; and
    a handle with open proximal and distal ends, the handle defining one or more helical grooves within a wall of the handle, wherein the inner sleeve containing the electrode assembly is slidably positioned within the handle such that each of the pins is slidably positioned in a respective one of the helical grooves and the rotary adjustment knob extends proximally of the open proximal end of the handle,
    wherein rotation of the rotary adjustment knob axially extends and axially retracts the electrode and the elongate barrel in relation to the handle.

2. The pacemaker device of claim 1, wherein the rotary adjustment knob is adjacent to a proximal end of the handle.

3. The pacemaker device of claim 1, further comprising a flange fixedly attached to a distal end portion of the handle.

4. The pacemaker device of claim 1, further comprising a releasable lock that is configured to latch the adjustment mechanism in a desired position.

5. The pacemaker device of claim 1, wherein the adjustment mechanism includes a telescoping arrangement, and wherein manipulation of the telescoping arrangement axially extends and axially retracts the electrode in relation to the handle.

6. A pacemaker system comprising:
a pacemaker device comprising:
- an electrode assembly including an electrode positioned at a distal end of an elongate barrel, wherein the electrode and the elongate barrel are electrically isolated from each other;
- one or more pins attached to and extending from the electrode assembly;
- an inner sleeve defining one or more longitudinal slots, wherein the electrode assembly is slidably positioned within the inner sleeve such that each of the pins extends through a respective one of the longitudinal slots;
- a rotary adjustment knob attached to a proximal end of the inner sleeve; and
- a handle,
- wherein rotation of the rotary adjustment knob axially extends and axially retracts the electrode and the elongate barrel in relation to the handle;

a transcutaneous electrode patch; and
an external automatic cardioverter defibrillator.

7. A method of delivering percutaneous temporary epicardial pacing for treating bradyarrhythmia of a patient, the method comprising:
- creating an incision in a skin surface of the patient;
- percutaneously installing a pacemaker device into the incision, wherein the installation results in the pacemaker device being positioned relative to the patient such that: (i) a distal portion of the pacemaker device including an electrode is positioned subcutaneously within the patient, (ii) a barrel portion of the pacemaker device extends through the incision, (iii) and a proximal portion of the pacemaker device including a handle is positioned externally of the patient, the pacemaker device having a sleeve within the handle, the sleeve slidably receiving the barrel and having an actuator extending from the sleeve and handle, wherein movement of the actuator causes rotation of the sleeve relative to the handle and extension of the barrel out of the sleeve;
- connecting the pacemaker device to an external automatic cardioverter defibrillator located externally of the patient; and
- providing pacing energy from the externally located external automatic cardioverter defibrillator to the patient via the percutaneously installed pacemaker device.

8. The method of claim 7, further comprising attaching a transcutaneous electrode to the skin surface of the patient and pacing a heart of the patient via the electrode of the pacemaker device and the transcutaneous electrode.

9. The method of claim 8, further comprising adjusting a depth of the electrode in relation to the skin surface of the patient.

10. The method of claim 7, wherein the electrode abuts an epicardial surface of a heart of the patient while providing the pacing energy.

* * * * *